(12) United States Patent
Sun et al.

(10) Patent No.: US 9,212,106 B2
(45) Date of Patent: Dec. 15, 2015

(54) RENEWABLE OLEFINS FROM A MIXTURE OF ACETIC ACID AND PROPIONIC ACID

(71) Applicants: Washington State University, Pullman, WA (US); ARCHER DANIELS MILDAND COMPANY, Decatur, IL (US)

(72) Inventors: Junming Sun, Pullman, WA (US); Changjun Liu, Pullman, WA (US); Yong Wang, Pullman, WA (US); Colin Smith, Pullman, WA (US); Kevin Martin, Mt. Zion, IL (US); Padmesh Venkitasubramanian, Forsyth, IL (US); Joshua Terrian, Lovington, IL (US)

(73) Assignees: Washington State University WA (US); Archer Daniels Midland Co., Decatur, IL (US)

( * ) Notice: Subject to any disclaimer, the term of this patent is extended or adjusted under 35 U.S.C. 154(b) by 154 days.

(21) Appl. No.: 14/105,249

(22) Filed: Dec. 13, 2013

(65) Prior Publication Data

US 2014/0128650 A1 May 8, 2014

Related U.S. Application Data

(63) Continuation-in-part of application No. PCT/US2013/062784, filed on Oct. 31, 2012.

(60) Provisional application No. 61/737,312, filed on Dec. 14, 2012, provisional application No. 61/720,433, filed on Oct. 31, 2012.

(51) Int. Cl.
*B01J 23/06* (2006.01)
*C07C 1/207* (2006.01)

(Continued)

(52) U.S. Cl.
CPC ............. *C07C 1/2078* (2013.01); *B01J 21/066* (2013.01); *B01J 23/06* (2013.01); *C07C 1/207* (2013.01); *C07C 5/327* (2013.01); *C07C 5/48* (2013.01); *C07C 29/00* (2013.01); *C07C 29/60* (2013.01);

(Continued)

(58) Field of Classification Search
CPC ...... C07C 1/2078; C07C 5/393; C07C 5/327; C07C 5/48; C07C 2/12; C07C 2521/06; C07C 2529/40; C07C 2523/06; C10G 3/00
USPC ................................................. 585/327, 638
See application file for complete search history.

(56) References Cited

U.S. PATENT DOCUMENTS

2011/0112344 A1* 5/2011 Chewter et al. ............... 585/302

OTHER PUBLICATIONS

Sun et al, Direct Conversion of Bio-ethanol to Isobutene on Nanosized ZnxZryOz Mixed Oxides with Balanced Acid—Base Sites ,Journal of the American Chemical Society, 2011, vol. 133, pp. 11096-11099.*

*Primary Examiner* — In Suk Bullock
*Assistant Examiner* — Philip Louie
(74) *Attorney, Agent, or Firm* — William B. Miller

(57) ABSTRACT

A process is described for making a product mixture including isobutene, propylene, 1-butene, 2-butene, 2-methyl-1-butene and 2-methyl-2-butene from a mixture of acetic acid and propionic and through reaction in the presence of a source of hydrogen and of a mixed oxide catalyst, for example, a $Zn_xZr_yO_z$ mixed oxide catalyst. A variety of commercially valuable products may be made in turn from the various $C_3$, $C_4$ and $C_5$ constituents of the product mixture.

14 Claims, 1 Drawing Sheet

(51) Int. Cl.
  *C07C 5/327* (2006.01)
  *C07C 5/48* (2006.01)
  *C10G 3/00* (2006.01)
  *B01J 21/06* (2006.01)
  *C07C 29/60* (2006.01)
  *C07C 51/235* (2006.01)
  *C07C 29/00* (2006.01)
  *C12P 7/52* (2006.01)
  *C12P 7/54* (2006.01)

(52) U.S. Cl.
  CPC ............... *C07C 51/235* (2013.01); *C10G 3/00* (2013.01); *C07C 2521/06* (2013.01); *C07C 2523/06* (2013.01); *C12P 7/52* (2013.01); *C12P 7/54* (2013.01)

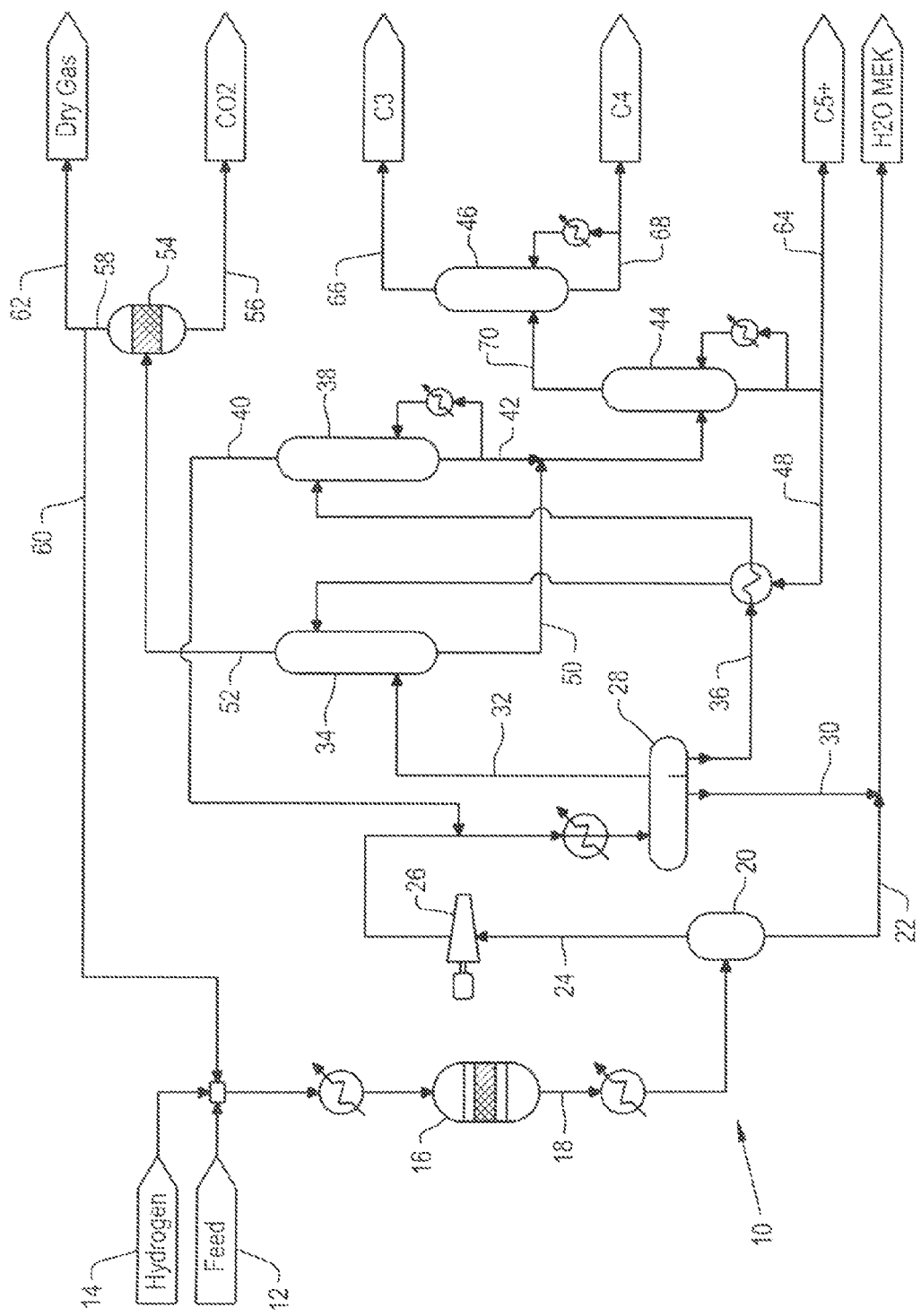

RENEWABLE OLEFINS FROM A MIXTURE OF ACETIC ACID AND PROPIONIC ACID

CROSS-REFERENCE TO RELATED APPLICATIONS

This application is a continuation-in-part of U.S. patent application Ser. No. 61/737,312 (the "'312 application"), filed Dec. 14, 2012 for "Process and Catalyst for Conversion of Acetic Acid to Isobutene", which in turn was filed as a continuation-in-part of U.S. Patent Application Ser. No. 61/720,433, filed Oct. 31, 2012 for "Stable Mixed Oxide Catalysts for Direct Conversion of Ethanol to Isobutene and Process for Making" (now Patent Cooperation Treaty Application No. PCT/US2013/062784 filed Oct. 1, 2013 (the "WO '784" application)). Both prior applications are incorporated by reference.

BACKGROUND

As related in the '312 application, isobutene is widely used for the production of a variety of industrially important products, such as butyl rubber for example. Isobutene has been produced commercially to date through the catalytic or steam cracking of fossil feedstocks, and the development of a commercially viable process for the manufacture of isobutene from a renewable source-based feedstock has accordingly become of great interest as fossil resources are increasingly depleted and/or have become more costly to use—especially in consideration of increased demand for isobutene.

Previous to the earlier WO '784 application, a hard-template method had been described for synthesizing $Zn_xZr_yO_z$ mixed oxides for the direct and high yield conversion of ethanol (from the fermentation of carbohydrates from renewable source materials, including biomass) to isobutene, wherein ZnO was added to $ZrO_2$ to selective passivate zirconia's strong Lewis acidic sites and weaken Brönsted acidic sites while simultaneously introducing basicity. The objectives of the hard template method were to suppress ethanol dehydration and acetone polymerization, while enabling a surface basic site-catalyzed ethanol dehydrogenation to acetaldehyde, an acetaldehyde to acetone conversion via aldol-condensation/dehydrogenation, and a Brönsted and Lewis acidic/basic site-catalyzed acetone-to-isobutene reaction pathway.

High isobutene yields were in fact realized, but unfortunately, as later experienced by Mizuno et al. (Mizuno et al., "One-path and Selective Conversion of Ethanol to Propene on Scandium-modified Indium Oxide Catalysts", Chem. Lett. vol. 41, pp. 892-894 (2012)) in their efforts to produce propylene from ethanol, it was found that further improvements in the catalyst's stability were needed.

The WO '784 application concerned the discovery that these improvements could be realized without adding modifying metals and without a reduction in the initial high activity (100 percent ethanol conversion) that had been observed in these mixed oxide catalysts, while the '312 application concerned the further discovery that the mixed oxide catalysts we had been evaluating for converting ethanol to isobutene are also able to catalyze the conversion of acetic acid to isobutene. Since acetic acid can be made by a variety of methods from a number of different starting materials, the capability of these mixed oxide catalysts to catalyze the conversion of acetic acid to isobutene enabled a range of options for utilizing renewable resources more efficiently, all as described in greater detail in the '312 application.

Separately, while commercial production of propionic acid to date has been entirely by petrochemical routes, a variety of proposed fermentation methods have been evaluated from as early as about 1920 for the industrial production of propionic acid, see Playne, "Propionic and Butyric Acids", Comprehensive Biotechnology: The Principles, Applications and Regulations of Biotechnology in Industry, Agriculture and Medicine, Volume 3, Pergamon Press, New York, N.Y. (1985) at pages 731-759, now incorporated by reference herein. One reason given by Playne for the absence of a commercial fermentation route to propionic acid is that acetic acid has been produced as a significant co-product. Bacteria listed by Playne as of "major importance" for the production of propionic acid from sugars, lactose or lactate through a dicarboxylic acid or acrylic acid metabolic pathway include *Propionibacterium*, especially *P. shermanii; Veillonella paroula; Veillonella alcalescens; Selenomonas ruminantium* (ph 5); *Selenomonas sputigena* (pH 5); *Clostridium propionicion Clostridium nomyi; Megasphaera elsdenii* (pH 4-8); *Bacteriodes fragilis; Bacteriodes riominicola*; and *Fusobacterium necrophoruni*.

Efforts to produce propionic acid by fermentation methods have continued in recent years, various approaches being described for producing propionic acid as well as some acetic acid in greater and lesser proportions from glucose, lactose, sucrose, xylose, fructose, maltose and lactate substrates. References describing these efforts include WO 2012/064883 to Yang et. al. (describing metabolically engineered organisms for producing propionic acid with increased yield and productivity, and increased tolerance to propionic acid and acidic pHs); Lewis and Yang, "Propionic acid fermentation by *Propionibacterium acidipropionici*: effect of growth substrate", Appl. Microbiol. Biotechnol., 37:437-442 (1992); Wang and Yang, "Propionic acid production in glycerol/glucose co-fermentation by *Propionibacterium freudenreichii* subsp. *Shermanii*", Bioresour. Technol., 137:116-123 (June 2013); and Zhang and Yang, "Engineering *Propionibacterium acidipropionici* for enhanced propionic acid tolerance and fermentation", Biotechnol. Bioeng., vol. 104, no. 4, pp. 766-773 (Nov. 1, 2009). Additional reduced biobased substrates, for example, glycerol, are taught as useful in some fermentations for improving the redox balance and the yield and selectivity to propionic acid.

The present invention concerns the still further discovery (to those reported in our previous '312 and WO '784 applications) that the same $Zn_xZr_yO_z$ mixed oxide catalysts—whether made by the hard template method or by the method of the WO '784 application—are also able, in the presence of hydrogen, to be used to produce several other olefins in addition to isobutene that are either of immediate commercial interest (e.g., propylene) or that can be readily upgraded by known methods to produce other valuable products, starting from a mixture of acetic and propionic acids as may be produced by known fermentation methods for the manufacture of propionic acid or in other ways accessible to those skilled in the art. Examples of the upgradeable olefins include the four-carbon products 1-butene and 2-butene, which can be used to make 1,3-butadiene, and the five-carbon products 2-methyl-1-butene and 2-methyl-2-butene, which can be used to make isoprene. Still other commercially interesting permutations will be apparent to those skilled in the art on consideration of the following summary and detailed description, for making products with biobased organic content that have historically been made exclusively from non-renewable resources.

SUMMARY OF THE PRESENT INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this in mind, in a first aspect, the present invention thus broadly concerns a process for making a product mixture including isobutene, propylene, 1-butene, 2-butene, 2-methyl-1-butene and 2-methyl-2-butene from a mixture of acetic acid and propionic acid through reaction in the presence of a source of hydrogen and of a mixed oxide catalyst, for example, $Zn_xZr_yO_z$ mixed oxide catalyst.

In a second aspect, the $Zn_xZr_yO_z$ mixed oxide catalyst can be an improved stability $Zn_xZr_yO_z$ mixed oxide catalyst prepared according to the WO '784 application.

In one embodiment, the 1-butene and 2-butene are separated from the product mixture and either or both are converted at least in part to 1,3-butadiene (CAS 106-99-0) by dehydrogenation or oxydehydrogenation using any of the known catalysts for performing this conversion, under conditions effective for carrying out the conversion.

In another embodiment, either or both of the 1-butene and 2-butene are converted by oxidation to products inclusive at least of maleic anhydride (CAS 108-31-6).

In another embodiment, either or both of the 1-butene and 2-butene are at least in part oligomerized to isooctene for use in a transportation fuel.

In another embodiment, at least a part of the 1-butene is hydroisomerized to provide additional 2-butene.

In another embodiment, at least some 2-butene (as present in the product mixture and/or from hydroisomerization of 1-butene) is combined with ethylene to yield additional propylene by olefin metathesis.

In another embodiment, at least some of the ethylene used for combining with 2-butene is derived through metathesis of 1-butene in the product mixture with itself.

In another embodiment, 2-butene in the product mixture and/or as formed by hydroisomerization of 1-butene in the product mixture is converted to additional isobutene (CAS 115-11-7) and propylene in the presence of a suitable catalyst examples of which are given below.

In another embodiment, isobutene in the product mixture is at least in part reverse isomerized to provide additional n-butene product.

In another embodiment, butadiene from the dehydrogenation or oxydehydrogenation of n-butene in the product mixture is at least in part polymerized by 1,2- and 1,4-addition with itself in the presence of a suitable catalyst to provide a polybutadiene polymer product.

In another embodiment, butadiene from the dehydrogenation or oxydehydrogenation of n-butene in the product mixture is at least in part chlorinated, and the resultant 1,4-isomers are isomerized before an alkaline dehydrochlorination step on the whole to provide a chloroprene product (CAS 126-99-8).

In another embodiment, butadiene from the dehydrogenation or oxydehydrogenation of n-butene in the product mixture is at least in part reacted with hydrogen cyanide sequentially in two steps to provide an adiponitrile product (CAS 111-69-3).

In another embodiment, adiponitrile so formed is at least in part catalytically hydrogenated to hexamethylenediamine (CAS 124-09-4).

In another embodiment, butadiene from the dehydrogenation or oxydehydrogenation of n-butene in the product mixture is at least in part converted to 1,4-butanediol (CAS 110-63-4) by any of several known methods for performing the conversion.

In another embodiment, butadiene from the dehydrogenation or oxydehydrogenation of n-butene in the product mixture is at least in part undergoes a 1,4-addition with itself to provide 4-vinylcyclohexene (CAS 100-40-3), which is subsequently dehydrogenated or oxidized to produce styrene (CAS 100-42-5).

In another embodiment, butadiene from the dehydrogenation or oxydehydrogenation of n-butene in the product mixture is at least in part used to provide improved impact resistance to polystyrene in the form of polybutadiene.

In another embodiment, butadiene from the dehydrogenation or oxydehydrogenation of n-butene in the product mixture is at least in part used as a monomer in an acrylonitrile-butadiene-styrene copolymer.

In another embodiment, butadiene from the dehydrogenation or oxydehydrogenation of n-butene in the product mixture is at least in part used as a monomer with methyl methacrylate and styrene in a copolymer.

In another embodiment, the 2-methyl-1-butene and 2-methyl-2-butene are separated from the reaction product and dehydrogenated to isoprene (CAS 78-79-5) using any of the known catalysts for performing this conversion, under conditions effective for carrying out the conversion.

In another embodiment, propylene in the product mixture is at least in part homopolymerized in the presence of a Ziegler-Natta catalyst or a metallocene catalyst to provide biobased polypropylene.

In another embodiment, propylene in the product mixture is at least in part converted to propylene oxide (CAS 75-56-9).

In another embodiment, propylene in the product mixture is at least in part converted, to acrylonitrile (CAS 107-13-1) by catalytic oxidation in the presence of ammonia.

In another embodiment, propylene in the product mixture is at least in part converted through catalytic oxidation to acrylic acid (CAS 79-10-7).

In another embodiment, propylene in the product mixture is at least in part converted to cumene (CAS 98-82-8) by reaction with benzene in the presence of a catalyst.

In another embodiment, propylene in the product mixture is at least in part hydrated to provide isopropanol (CAS 67-63-0), indirectly through reaction with sulfuric acid and subsequent hydrolysis of the resultant sulfate esters and/or directly by reaction with water in a liquid or gas phase process in the presence of a suitable catalyst.

In still other embodiments, two or more of these various individual end uses or product scenarios are concurrently practiced.

BRIEF DESCRIPTION OF THE DRAWING

FIG. 1 schematically illustrates a process of the present invention according to one embodiment, including one possible approach that may be taken for separating the product mixture produced by the process of the present invention according to a first aspect.

DETAILED DESCRIPTION OF PREFERRED EMBODIMENTS

Those skilled in the art will immediately appreciate from the foregoing summary that the capacity to produce, by means of the process of the present invention, a product mixture including isobutene, propylene, 1-butene, 2-butene, 2-methyl-1-butene and 2-methyl-2-butene from a mixture of acetic acid and propionic acid provides opportunity to impart renewable content to a variety of commercially valuable materials that that have historically been made exclusively from non-renewable resources, as well as an additional method for imparting renewable content to the making of other commercially valuable materials where other means have been previously suggested for this purpose, but these other known processes may not be fully satisfactory for one reason or another.

Some of these commercially valuable materials are expressly addressed by the various embodiments mentioned in the summary section above, but the realization of other products—for example, methyl methacrylate, tetrahydrofuran, N-vinylpyrrolidinone, laurylactam, adipic acid, caprolactam, ethylidene norbornene among others, along with associated renewable polymers and copolymers—will be within the capabilities of those skilled in the art, as demonstrated by US 2010/0216958 A1 to Peters et al, published Aug. 26, 2010 for "Methods of Preparing Renewable Butadiene and Renewable Isoprene" (hereafter "Peters et al."), now incorporated herein by reference.

Those skilled in the art will concurrently also appreciate, in view of the extensive body of literature descriptive of the means by which the upgradeable olefins in the product mixture may be used individually, in combination with one or more other constituent materials of the product mixture and/or in combination with still other materials not in the product mixture but which may be readily available nonetheless—for example, ammonia for combining with the propylene to prepare acrylonitrile, benzene for combining with propylene to prepare cumene or hydrogen cyanide for combining with 1,3-butadiene (from the 1-butene and/or 2-butene) to prepare adiponitrile—to prepare these various commercially valuable materials, that a comprehensive review of all of the many commercially valuable materials that can be made (at least in part) from the upgradeable renewable source-derived olefins in the product mixture and of the ways in which the upgradeable olefins in the product mixture can be utilized to make the commercially valuable materials is neither feasible nor truly necessary in light of what is known to those skilled in the art.

Accordingly, while certain applications of the upgradeable olefins in the product mixture will be described herein (by reference to exemplary publications within that extensive body of literature), it will be appreciated that these are intended to be illustrative only.

Turning now to FIG. 1, a process 10 is schematically illustrated wherein a mixed acid feedstock 12 comprising both acetic acid and propionic acid, but preferably having acetic acid and propionic acid as the two most prevalent acids therein, is combined with hydrogen 14 and converted in a reactor 16 containing a catalyst, particularly, a $Zn_xZr_yO_z$ mixed oxide catalyst, to a product mixture 18 having an upgradeable olefins component including isobutene, propylene, 1-butene, 2-butene, 2-methyl-1-butene and 2-methyl-2-butene as well as a remainder including water, acetone, methyl ethyl ketone (or 2-butanone, henceforth MEK), methane and carbon dioxide. Under certain conditions as shown by the examples below, six-carbon products may be formed as well, but in preferred embodiments substantially no six-carbon and heavier products will be formed.

The mixed acid feedstock 12 in the illustrative embodiment of FIG. 1 may be produced by those known fermentation methods to propionic acid from glucose, lactose, sucrose, xylose, fructose, maltose and lactate substrates (as previously described) which also produce some acetic acid, by a combination of propionic acid from a known fermentation method with acetic acid from a separate, known method of making acetic acid (various such methods are described in the '312 application), or by a combination of propionic acid from a known fermentation method with acetic acid from a separate, known method or source of acetic acid and with recycle acetic acid produced in certain upgrading options from the product mixture 18—for example, in the oxidation of some part of the n-butenes in the product mixture 18 in the presence of steam, see, e.g., U.S. Pat. No. 3,431,297.

While a single fermentation may thus be employed to provide a mixed acid feedstock 12, both because of the well-appreciated difficulties associated with mixed acid fermentations generally and because of the improved flexibility afforded to provide mixed acid feedstocks 12 of differing compositions, it is expected that preferably separate fermentations will be employed to preferentially generate propionic acid on the one hand (building upon some of the above-referenced recent advancements in propionic acid fermentations, for example and acetic acid on the other. The propionic acid and acetic acid can then be conventionally recovered from the individual fermentation broths and recombined to provide a mixed acid feedstock 12, or acetic acid or propionic acid can be recovered from its respective fermentation broth for combining into the other fermentation broth to yield the mixed acid feedstock 12, or the individual broths from the two fermentations can be combined to provide the mixed acid feedstock 12.

The production of acetic acid by fermentation fits very well with an independent fermentation mode of generating the mixed acid feedstock 12, in that various homoacetogenic microorganisms are known which are able through fermentation to produce acetic acid with 100% carbon yield; these microorganisms internally convert carbon dioxide to acetate, in contrast to a process for producing ethanol from sugars obtained from biomass, wherein carbon dioxide is produced as a byproduct.

Examples of homoacetogens given by U.S. Pat. No. 8,252,567 are microorganisms of the genus *Moorella* and *Clostridium*, especially microorganisms of the species *Moorella thermoaceticum* (described as formerly classified as *Clostridium thermoaceticum*) or *Clostridium formicoaceticum*. U.S. Pat. No. 8,252,567 represents that about one hundred known acetogens in twenty-two genera were known as of 2009, and cross-references Drake, et al., Ann. NY Acad. Sci. 1125: 100-128 (2008) for a review of acetogenic microorganisms.

Other references describing fermentation methods for producing acetic acid from five and six carbon sugars include U.S. Pat. No. 4,935,360; U.S. Pat. No. 8,236,534; U.S. Pat. No. 4,513,084; U.S. Pat. No. 4,371,619 and U.S. Pat. No. 4,506,012; both one-step fermentation processes from the sugars to acetic acid acetates or both are disclosed, as well as two-step processes involving a first fermentation to lactic acid (by lactobacillus or known methods of homolactic fermentation, preferably) followed by a second fermentation to convert lactic acid to acetic acid, for example, using *Clostridium formicoaceticum*.

Any of the known fermentation methods may, in short, be used to produce acetic acid for combining with propionic acid in the mixed acid feedstock 12, but homoacetogenic fermentation methods are considered preferable at least in that carbon dioxide is not produced as a byproduct—the carbon dioxide represents a yield loss from the overall process to make isobutene and as a greenhouse is undesirable particularly in the context of a process to make a needed product more sustainably from renewable resources.

The mixed acid feedstock 12 can in other embodiments be provided in whole or in part without the use of fermentation methods, for example, from the dehydration and oxidation of 1,2-propanediol (propylene glycol) and ethylene glycol obtained by the hydrogenolysis of a feedstock selected from one or more of glycerol, the five and six carbon sugars and sugar alcohols, lactate and lactic acid in the presence of hydrogen and a suitable hydrogenolysis catalyst and under conditions which are effective for carrying out the hydrogenolysis. More particularly, ethylene glycol produced in such a process can be dehydrated and then the product of that dehydration step can be oxidized to provide acetic acid for the mixed acid feedstock 12, while propylene glycol from the hydrogenolysis process can be dehydrated, and the product of the dehydration step then likewise oxidized to propionic acid for the mixed acid feed 12.

Propylene glycol and ethylene glycol have conventionally been produced from petrochemical sources. However, in recent years much research has taken place to develop suitable biobased propylene glycol and ethylene glycol products, which can be interchangeable with propylene glycol and ethylene glycol products deriving from petroleum refining and processing methods but which are made from renewable versus nonrenewable materials.

As a result of these efforts, processes have been developed by several parties involving the hydrogenolysis of especially five and six carbon sugars and/or sugar alcohols, whereby the higher carbohydrates are broken into fragments of lower molecular weight to form compounds which belong to the glycol or polyol family. Sugars containing five carbon chains, such as ribose, arabinose, xylose and lyxose, and corresponding five carbon chain sugar alcohols such as xylitol and arabinitol, are among the materials contemplated in U.S. Pat. No. 7,038,094 to Werpy et al., for example, as are lactic acid, lactate and six carbon sugars such as glucose, galactose, maltose, lactose, sucrose, allose, altrose, mannose gulose, idose and talose and six carbon chain sugar alcohols such as sorbitol. Some of these carbohydrate-based feedstocks are commercially available as pure or purified materials. These materials may also be obtained as side-products or even waste products from other processes, such as corn processing. The sugar alcohols may also be intermediate products produced in the initial stage of hydrogenating a sugar.

For other known examples of such processes, U.S. Pat. No. 5,206,927 describes a homogeneous process for hydrocracking carbohydrates in the presence of a soluble transition metal catalyst to produce lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi. However, as is evident from Tables II and III in the disclosure of U.S. Pat. No. 5,206,927, about 2-7% of other polyol compounds are produced in the hydrocracking process. U.S. Pat. No. 4,476,331 describes a two stage method of hydrocracking carbohydrates using a modified ruthenium catalyst. European Patent Applications EP-A-0523 014 and EP-A-0 415 202 describe a process for preparing lower polyhydric alcohols by catalytic hydrocracking of aqueous sucrose solutions at elevated temperature and pressure using a catalyst whose active material comprises the metals cobalt, copper and manganese. Still other examples of such carbohydrate-based processes may be found without difficulty by those skilled in the art.

Other efforts have been based on the use of another readily accessible biobased feedstock, namely, glycerol. The aforementioned. U.S. Pat. No. 7,038,094 to Werpy et al. describes the hydrogenolysis of glycerol as well over rhenium-containing catalysts, as an example, but a number of references may be found related to the hydrogenolysis of glycerol to produce biobased propylene glycol as well as ethylene glycol.

Glycerol is currently produced as a byproduct in making biodiesel from vegetable and plant oils, through the transesterification reaction of lower alkanols with higher fatty acid triglycerides to yield lower alkyl esters of higher fatty acids and a substantial glyercol byproduct. Glycerol is also available as a byproduct of the hydrolysis reaction of water with higher fatty acid triglycerides to yield soap and glycerol. The higher fatty acid triglycerides may derive from animal or vegetable (plant) sources, or from a combination of animal and vegetable sources as well known, and a variety of processes have been described or are known. A biobased glycerol is also available as a product of the hydrogenolysis of sorbitol, as described in an exemplary process in U.S. Pat. No. 4,366,332, issued Dec. 28, 1982.

A biobased ethylene glycol and propylene glycol in any event may be converted to acetic acid and propionic acid, respectively, for the mixed acid feedstock 12 by first dehydrating the ethylene glycol and propylene glycol to their corresponding aldehydes acetaldehyde and propionaldehyde, then oxidizing the acetaldehyde and propionaldehyde to provide acetic acid and propionic acid. Various catalysts for the dehydration of propylene glycol (1,2-propanediol) have been evaluated, and are available from the prior art, see, for example. Mori et al., "Catalytic dehydration of 1,2-propanediol into propanal", Applied Catalysis A: General, vol. 366 pp. 304-308 (2009) (finding acidic inorganic oxides and supported heteropolyacids useful for a vapor phase dehydration, especially, silica-supported heteropolyacids with an aqueous propylene glycol feed); Sugiyama et al., "The Catalytic Conversion, of 1,2-Propanediol to Propanal on FSM-16 Molded by Wet-Treatment and Pressurization", Journal of Chemical Engineering of Japan, vol. 46, no. 9, pp 620-624 (2013)(FSM-16 being described as a mesoporous silica); Cherysheva et al., "Nature of the Products from the Catalytic Dehydration of Propylene Glycol", Zhurnal Organicheskoi Khimii, vol. 7, no. 1, p. 212 (January 1971)(cation-exchange resins, p-toluenesulfonic acid and sulfuric acid); and Zhang et al., "Dehydration of 1,2-propanediol to propionaldehyde over zeolite catalysts", Applied Catalysis A: General, vol. 400, pp 148-155 (2011) (discussing prior studies with electrophilic, nucleophilic and lanthanide oxide catalysts in evaluating (and finding effective) zeolites such as ZSM-5). A number of examples of the dehydration of ethylene glycol to acetaldehyde are similarly available in the prior art, as referenced and summarized by Smith, "Ethylene glycol to acetaldehyde—dehydration or a concerted mechanism", Tetrahedron, vol. 58, pp. 2091-2094 (2002). Parenthetically, it is contemplated that the dehydrations of propylene glycol and of ethylene glycol can be done on a mixture of the glycols, or on the propylene glycol and ethylene glycol separately and independently.

The subsequent oxidation of the acetaldehyde and propionaldehyde dehydration products to provide acetic and propionic acids can be done by any conventionally known oxidation method. In this regard, as described in Sano et al., "Acetic acid production by direct oxidation of ethylene", Chem. Eng. Technol., vol. 29, no. 11, pp. 1376-1380 (2006), the primary method for producing acetic acid commercially for many years was by oxidation of acetaldehyde in the presence of a manganese acetate catalyst, though this method has now been supplanted by carbonylation of methanol. Catalytic methods for the oxidation of propionaldehyde to yield propionic acid have likewise, been described, which have principally involved vanadium oxide and vanadium phosphate catalysts, see Slavucha et al., Catal. Lett., No. 2, page 257 (1989)

and Ai et al., Bull. Chem. Soc. Jpn. no. 67 pg. 551 (1994), the oxidation of a mixture of acetaldehyde and propionaldehyde has likewise been described on a titania-supported vanadium oxide catalyst in the presence of water vapor, see Suprun et al., Chem. Eng. Technol., vol. 29, no. 11, pp 1376-1380 (2006). Consequently, it is contemplated that the oxidation step can likewise be conducted on a mixture of the acetaldehyde and propionaldehyde dehydration products or on the acetaldehyde and propionaldehyde individually, but those skilled in the art will be well able in any event to determine how best to conduct the dehydration and oxidation steps on the ethylene glycol and propylene glycol from a preceding hydrogenolysis process in order to provide the acetic and propionic acids for mixed acid feedstock 12.

However obtained, the mixed acid feedstock 12 is combined with hydrogen 14 and converted to the product mixture 18 including the upgradeable olefins fraction. In a first embodiment, a $Zn_xZr_yO_x$ mixed oxide catalyst useful for the conversion of the acetic acid and propionic acid in the mixed acid feedstock 12 as described can be made by a "hard template" or "confined space synthesis" method generally of the character used by Jacobsen et al., "Mesoporous Zeolite Single Crystals", Journal of the American Chemical Society, vol. 122, pp. 7116-7117 (2000), wherein nanozeolites were prepared.

More particularly, the same carbon black (BP 2000, Cabot Corp.) may be used as a hard template for the synthesis of nanosized $Zn_xZr_yO_z$ mixed oxides, rather than nanozeolites as in Jacobsen et al. Prior to use, the BP 2000 template is dried, for example, at 180° C. overnight. Calculated amounts of zirconyl nitrate hydrate (Sigma-Aldrich, greater than 99.8% purity) and $Zn(NO_3)_2 \cdot 6H_2O$ (Sigma-Aldrich, greater than 99.8% purity) are dissolved in a given amount of water, and sonicated for 15 minutes to produce a clear solution with desired concentrations of Zn and Zr. In one preparation, about 25 grams of the obtained solution are then mixed with 6.0 grams of the preheated BP 2000 to achieve incipient wetness, and the mixture is transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders are obtained, having a mean particle size of less than 10 nanometers.

The nanosized $Zn_xZr_yO_z$ mixed oxide catalysts made by a hard template method are further described in Sun et al., "Direct Conversion of Bio-ethanol to Isobutene on Nanosized $Zn_xZr_yO_z$ Mixed Oxides with Balanced Acid-Base Sites", Journal of the American Chemical Society, vol. 133, pp. 11096-11099 (2011) along with findings related to the character of the mixed oxide catalysts formed thereby and the performance of the catalysts for the ethanol to isobutene conversion, given certain Zn/Zr ratios, residence times and reaction temperatures.

Alternatively, the $Zn_xZr_yO_z$ mixed oxide catalysts may be made as described in copending U.S. Patent Application Ser. No. 61/720,433, filed Oct. 31, 2012 for "Stable Mixed Oxide Catalysts for Direct Conversion of Ethanol to Isobutene and Process for making" (the WO '784 application), by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined.

In certain embodiments, the $Zn_xZr_yO_z$ mixed oxide catalysts (whether made by the hard template or incipient wetness methods) are characterized by a Zn/Zr ratio (x:y) of from about 1:100 to about 10:1, preferably from about 1:30 to about 1:1, especially about 1:20 to about 1:5, and still more preferably about 1:12 to about 1:10.

The catalysts made by the alternative, incipient wetness method are consistent in their particle size with the catalysts described in the incorporated journal article, namely, comprising aggregates of less then 10 nm-sized particles with a highly crystalline structure. The Zn oxide component is again highly dispersed on the Zr oxide component.

In certain embodiments, the $Zn_xZr_yO_z$ mixed oxide catalysts are characterized as to sulfur catalysts, containing less than about 0.14 percent by weight of sulfur. In the WO '784 application, it was reported in the context of converting ethanol to isobutene that catalysts made by the incipient wetness method would desirably be substantially sulfur-free, preferably including less than about 0.01 percent by weight of sulfur and more preferably including less than about 0.001 weight percent of sulfur. In the WO '784 application, it was postulated that the reduced sulfur content enabled by the incipient wetness method as compared to the hard template method contributed significantly to the much improved stability observed for the incipient wetness method catalysts of the prior related application for the ethanol to isobutene process.

In the particular context of the '312 application (for converting acetic acid to isobutene), however, in at least some embodiments and under certain process conditions some sulfur did appear to be beneficial. Since the process of the present invention is concerned with the processing of a mixed acid feedstock 12 containing acetic acid, it is anticipated that again there may be benefit to not having the catalyst be substantially sulfur-free as preferred in the WO '784 application, though as just indicated, it is expected that the amount of sulfur will preferably be such that the catalysts are still characterized as low sulfur catalysts. Such low sulfur catalysts are most readily made by the incipient wetness method described briefly above and in greater detail in the WO '784 application.

In principle, provided the zinc and zirconium compounds and solids in these embodiments have a sufficiently low sulfur content in order to produce a low sulfur content when combined according to the incipient wetness method, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining. Low sulfur catalysts can also be made by the incipient wetness method starting with zinc and zirconium compounds that are sulfur-free or substantially sulfur-free, then doping in a desired sulfur content into the $Zn_xZr_yO_x$ mixed oxide catalysts.

The conditions and times for the drying and calcining steps of an incipient wetness preparation will depend, of course, on the particular zinc and zirconium materials and solvent used, but in general terms, the drying step can be accomplished in a temperature range of from about 60 degrees Celsius to about 200 degrees Celsius over at least about 3 hours, while the calcining can take place at a temperature of from about 300 degrees Celsius to about 1500 degrees Celsius, but more preferably a temperature of from about 400 to 600 degrees Celsius is used. The calcination time can be from about 10 minutes to about 48 hours, with from about 2 to about 10 hours being preferred.

In still other embodiments, low sulfur catalysts could be prepared by a hard template method, except that a suitably very low sulfur content carbon is used for the hard template to realize a low sulfur content in the finished catalyst.

In certain embodiments, the conversion of the acetic acid and propionic acid in mixed acid feed 12 to the product mixture 18 can be accomplished continuously in the gas phase, using a fixed bed reactor or flow bed reactor. The reaction temperature may be in a range from about 200 to about 700 degrees Celsius, preferably, in a range from about 300 to about 500 degrees Celsius, and the WHSV can be in a range from about 0.01 hr to about 10 $hr^{-1}$, preferably from about 0.05 $hr^{-1}$ to about 2 $hr^{-1}$. Acetic/propionic acid/water solutions with steam to carbon ratios from 0 to 20, preferably from 2 to 5 can be used to provide the acetic and propionic acids to the catalyst.

Hydrogen is supplied from a source 14, generally in combination with an inert carrier gas such as nitrogen. As demonstrated by the examples below, by adjusting the partial pressure of hydrogen in the reactor (all other conditions remaining the same), different product distributions can be produced of the various upgradeable olefins in the product mixture 18 as desired, based on the manufacturer's requirements at any given time. Further, this effect can be made greater or lesser or even manifested in a different way, depending on the particular reaction conditions employed. The examples in particular show that the effects of the same partial pressure changes were quite different on an equimolar mixture of the acetic and propionic acids as compared to a high acetic:propionic mixture; notably, increased hydrogen partial pressures in converting the equimolar mixture resulted in increased selectivity to isobutene, 1-butene and 2-butene while the same partial pressure changes in converting the high acetic:propionic mixture resulted in decreasing selectivity on the whole to these $C_4$ products. The magnitude of the selectivity effects for the propylene and $C_5$ products (2-methyl-2-butene, 2-methyl-1-butene, 2-pentene) in the product mixture also differed, particularly relating to the amount of propylene produced.

The product mixture 18 in the particular embodiment of FIG. 1 is then cooled and passed to a knockout drum 20 to remove water and to remove acetone and MEK solubilized therein via, stream 22 from the mixture 18. The remainder 24 is passed to is wet gas compressor 26, further cooled and sent to a high pressure receiver 28. Additional water, acetone and MEK is removed via stream 30 from the product mixture 18, and lighter components than the desired upgradeable olefins—methane, unreacted hydrogen and carbon dioxide—are mostly conveyed in stream 32 to a sponge absorber 34. The heavier components of the product mixture, including the bulk of the desired upgradeable olefins, are meanwhile sent in stream 30 to a stripper 38.

In the stripper 38, residual methane, hydrogen and carbon dioxide not separated into stream 32 from the high pressure receiver 28 are stripped away in stream 40 from the propylene, $C_4$ and $C_5$ (and $C_6$, if any) products to which proceed in stream 42 to a debutanizer 44 and depropanizer 40 in sequence. Stream 40 is recycled to the high pressure receiver 28 to capture any propylene into the stream 36, with capturing the residual gases into stream 32 on recycle.

The 2-pentene, 2-methyl-1-pentene and 2-methyl-2-pentene from product mixture 18 are separated (together with any $C_6$ products, but preferably there will be substantially no $C_6$ products) in the debutanizer 44 from the propylene, isobutene, 1-butene and 2-butene upgradeable olefins, with a portion 48 of the 2-pentene, 2-methyl-1-pentene and 2-methyl-2-pentene materials being recycled to the sponge absorber for efficiently separating any propylene ($C_3$), isobutene, 1-butene and 2-butene ($C_4$) content in stream 32 from the lighter gases contained in product mixture 18, though other absorbents could be used in place of a recycle portion 48. The $C_3$ and $C_4$ products recovered into the $C_5$ recycle portion 48 proceed from the absorber 34 (with the $C_5$ recycle absorbent) as stream 50, and stream 50 including the recycled $C_5$ products is then combined with primary $C_3$-$C_5$ stream 42 from the stripper 38 for processing in the debutanizer/depropanizer section, while the methane, unreacted hydrogen and carbon dioxide are carried overhead from the sponge absorber 34 as stream 52 to a pressure swing absorption unit 54.

Pressure swing absorption unit 54 operates to separate carbon dioxide 56 from a dry gas 58 comprised of methane and unreacted hydrogen. If the hydrogen content of the dry gas 58 is substantial enough, the dry gas 58 may be recycled in whole or in part as recycle gas stream 60 to provide makeup hydrogen for use in the reactor 16, or may be used as a fuel gas 62 or for other suitable purposes.

The debutanizer 44 and depropanizer 46 operate in sequence to produce the 2-pentene 2-methyl-1-butene and 2-methyl-2-butene in debutanizer bottoms ($C_5$) product 64, with a propylene ($C_3$) product 66 and an isobutene, 1-butene and 2-butene ($C_4$) product 68 from the overheads 70 from debutanizer 44.

The $C_3$, $C_4$ and $C_5$ products can be used, as already observed, to provide a significant number of commercially valuable products, following such further conventional refining as may be indicated for the $C_4$ and $C_5$ products to upgrade individual materials within these products to certain commercially important products.

For example, in one embodiment, the isobutene can be separated from the n-butenes in the $C_4$ product 68. Though the separation of isobutene from 1-butene and 2-butene is not facile, methods are known for performing the separation, see "Butenes", Ullmann's Encyclopedia of Industrial Chemistry, 11th ed., Wiley-VCH Verlag GmbH & Co. KGaA Weinheim (2012) at pages 445-455 and the references cited therein. See also, U.S. Pat. No. 8,293,960 to Arnold et al., "Process for the Production of Butadiene" (describing isomerization of 1-butene to 2-butene with distillation, and an optional reverse isomerization to convert isobutene to additional n-butenes as desired, for additional 1,3-butadiene or other products derived, from the n-butenes versus isobutene) and U.S. Pat. No. 8,025,857 to Gartside et al. for "Apparatus for the Double Bond Hydroisomerization of Butenes" (describing hydroisomerization of 1-butene to 2-butene in a mixed $C_4$ stream, followed by distillation to produce a butadiene process feed and additionally describing making propylene from 2-butene by combination with ethylene and through olefin metathesis); see also U.S. Pat. No. 7,888,541 to Gartside et al., "Double Bond hydroisomerization of Butenes". The isobutene is itself a commercially valuable material, being widely used for the production of a variety of industrially important products, such as butyl rubber for example.

Alternatively the isobutene can be converted to biobased fuel additives, in particular, ethyl and methyl tertiary butyl ethers (ETBE and MTBE, respectively). Conventionally MTBE has been made in petroleum processing, in integrated processes for the production from a mixed $C_4$ stream from petroleum crackers (after removal of multiply unsaturated hydrocarbons such as butadiene) of isobutene as used in making, butyl rubber, polyisobutylene, isobutene oligomers and t-butyl aromatics, of tert-butanol (TBA) and MTBE in desired proportions. The art contains a number of examples of such integrated processes for making non-biobased, conventional MTBE, see, for example, U.S. Pat. No. 4,118,425 to Herbstman U.S. Pat. No. 4,329,516 to Al-Muddarris, U.S. Pat. No. 4,423,251 to Pujado et al., U.S. Pat. No. 4,981,491 to Harandi et al., and U.S. Pat. No. 5,254,764 to Miracca et al., as well as Ullmann's Encyclopedia of Industrial Chemistry, 11th ed., "Methyl Tert-Butyl Ether", pp 119-130, Wiley-VCH Verlag GmbH & Co. KGaA Weinheim (2012). ETBE for its part has been made in a like manner as MTBE, through using ethanol rather than methanol in the etherification step of such processes.

In another alternative embodiment, the isobutene can be used in whole or in part to make isoprene according to any of a number of known processes. Conventionally, isoprene has been recovered from pyrolysis gasoline in naphtha cracking to produce ethylene, by a series of fairly capital intensive steps. Initially cyclopentadiene is removed from the pyrolysis gasoline by dimerization and distillation. Subsequently, pipirylenes are separated out by superfractionation, and the isoprene (at 10 to 20% of the pyrolysis gasoline) is then recovered by extractive distillation using a solvent. In recent years, however, with the availability of abundant, inexpensive natural gas, ethylene has increasingly been produced using lighter feedstocks for the steam crackers so that pyrolysis gasoline production has declined.

As summarized in WO 2012/038247 A1 by Vermeiren et al., "Production of Isoprene from Iso-Butanol" (WO '247), isoprene can be produced by a Prins condensation of a $C_4$ olefin feed with an aldehyde, typically formaldehyde, with the $C_4$ olefin feed commonly including isobutene or one or more isobutene precursors such as an alkyl-t-butyl ether under conditions which will provide isobutene. The isobutene reacts with formaldehyde to give 4,4-dimethyl-m-dioxane which decomposes to provide the desired isoprene product.

WO '247 reports a number of other examples of processes of this general character. For example, U.S. Pat. No. 4,511,751 describes a process wherein isobutene and/or tertiary butanol and a formaldehyde source are fed, together with water, into an acidic aqueous solution continuously or intermittently while maintaining the reaction pressure in an adequate range and at the same time distilling off the isoprene product and unreacted starting materials, together with water, from the reaction zone. U.S. Pat. No. 4,593,145 is cited for describing a process for producing isoprene, characterized in that an alkyl-t-butyl ether (e.g., methyl-t-butyl ether (MTBE) or ethyl-t-butyl ether (ETBE) as are still commercially manufactured and extensively used as antiknock fuel additives) and a formaldehyde source are fed, together with water, into an acidic aqueous solution continuously or intermittently while maintaining the reaction pressure in an adequate range and at the same time distilling off the product isoprene, unreacted starting materials, isobutene and tertiary butanol, together with water, from the reaction zone. Other cited examples include EP 106123, EP 1614671, EP 2157072 GB 1370899 and U.S. Pat. No. 3,972,955.

It is also known to directly produce isoprene from tertiary alkyl ethers (such MTBE) and an oxygen source by a catalytic process. For example, in U.S. Pat. No. 3,374,780 isoprene is produced by passing a mixture of MTBE and air over a mixed oxide catalyst, cracking the MTBE to isobutene and methanol, oxidizing the methanol to formaldehyde and then reacting the isobutene and formaldehyde to produce isoprene. Other references supply isobutene and methanol separately. The methanol is oxidized to formaldehyde alongside methanol generated from the cracking of MTBE, and the formaldehyde so formed reacts with the supplied isobutene plus that isobutene generated from the cracking of MTBE. Still other references supply isobutene and methanol directly rather than generating the same by cracking MTBE, oxidizing the methanol to formaldehyde with an oxygen source in the presence of an oxidation catalyst and then reacting the formaldehyde thus formed with the isobutene feed.

Consequently, it will be appreciated from the summary of these various known methods that isoprene can in certain embodiments be produced from the isobutene in stream 68, as well as from the MTBE that can be made from the isobutene.

Isoprene can also be made by the 2-methyl-1-butene and 2-methyl-2-butene upgradeable olefins in the debutanizer bottoms product 64. The WO'247 reference thus also describes that isoprene can be produced in a conventional petroleum refinery setting by the isolation of isoamylenes (principally being the same 2-methyl-1-butene and 2-methyl-2-butene materials) from refinery and petroleum cuts and then converting the isoamylenes to isoprene over an iron oxide catalyst promoted with potassium compounds.

U.S. 2010/0022816 to Merrill alternatively describes a process wherein 2-methyl-1-butene and 2-methyl-2-butene are combined with steam and contacted with a dehydrogenation catalyst under conditions effective to produce isoprene, with preferred embodiments carried out under a vacuum at a pressure of 1,000 mbar or less.

Returning now to the 1-butene and 2-butene upgradeable olefin products in stream 68, in one embodiment, these may be converted to 1,3-butadiene by catalytic dehydrogenation or catalytic oxidative dehydrogenation according to known methods, see"Butadiene", Ullmann's Encyclopedia of Industrial Chemistry, $11^{th}$ edition, Wiley-VCH Verlag GmbH & Co. KGaA, Wertheim (2012) at pages 381-396 and the references cited therein, especially page 387 and references 44-47; GB 602,499 (Phillips Petroleum Company) and GB 649,444 (Standard Oil).

The 1,3-butadiene thus formed can in other embodiments be used to produce in whole or in part to produce other commercially valuable products, again according to known methods. Thus, as further described in the just-referenced "Butadiene" article, the 1,3-butadiene can be used as a monomer or co-monomer in the manufacture of various synthetic rubbers, e.g., styrene-butadiene rubber and latex polybutadiene rubber, acrylonitrile-butadiene rubber and latex, and chloroprene rubber. Important plastics containing, butadiene as a monomer component are impact-resistant polystyrene, as two-phase system consisting of polystyrene and polybutadiene, acrylonitrile/butadiene/styrene (ABS) polymers, and a copolymer of methyl methacrylate butadiene and styrene.

The 1,3-butadiene can in other embodiments be used to make still other products. US 2010/0216958 to Peters et al. ("Peters et al.), which is hereby incorporated by reference herein, is descriptive of methods for preparing renewable butadiene and renewable isoprene, albeit starting from $C_4$ and $C_5$ alcohols through dehydration to $C_4$ and $C_5$ olefins which are then converted to isobutene, isoprene and butadiene by dehydrogenation. As described in Peters, 1,3-butadiene can be used to make 1,4-butanediol and/or tetrahydrofuran (page 7, paragraph 56), and these can then be used to turn to make additional polymer products, as well as gamma-butyrolactone, N-methylpyrrolidinone and N-vinylpyrrolidinone.

The 1,3-butadiene can also be used to prepare nylon-6,6 and nylon-6 polymers (Peters, paragraphs 61 and 62), in the former instance by reacting butadiene with HCN in the presence of a zero valent nickel catalyst to provide adiponitrile. The adiponitrile can be hydrogenated to form hexamethylenediamine, and hydrolyzed to form adipic acid. The hexamethylenediamine and adipic acid can be polymerized to form the nylon-6,6 polymer. Alternatively, the adiponitrile can be hydrocyanated and cyclized to caprolactam, referencing U.S. Pat. No. 5,801,286 and U.S. Pat. No. 5,693,793, which can then be polymerized to a nylon-6 polymer.

Peters also describes, at paragraph 64, that the 1,3-butadiene can be used to prepare renewable styrene, polystyrene and styrenic polymers. For example, 1,3-butadiene can be dimerized to vinylcyclohexene, which can be dehydrogenated in stepwise fashion to form ethyl benzene and then styrene. Alternatively, the vinylcyclohexene can be dehydrogenated directly to styrene.

The 1,3-butadiene in still another embodiment can undergo cyclotrimerization to form 1,5,9-cyclododecatriene (CDT), for example, as described U.S. Pat. No. 8,168,841 to Herwig at al. or any of a number of known processes referenced by Herwig et al. and elsewhere. As with non-renewable CDT from conventional butadiene, the CDT may be brominated to make flame retardants and used to prepare lactams, lauryllactam, for being polymerized to a renewable nylon-12 (or for being used as a monomer in other polymers), or for preparing 1,12-dodecanedioic acid which is a known commercially useful dicarboxylic acid.

Peters relates other uses that can be made of the isobutene, as well, including methylmethacrylate, methacrylic acid and methacrylic acid esters generally, see para. 68 of Peters.

The 1-butene and 2-butene products can likewise be used in still other ways, as described, for example, in the "Butenes" article referenced above and in the various publications cited in the "Butenes" article. Briefly, however, the butenes can be placed to the same uses as found for the non-renewable butenes; for alkylate gasoline, polymer gasoline, as a plant fuel or simple fuel blendstock, for 1-butene as a co-monomer in linear low density polyethylene and high density polyethylene.

The 1-butene and 2-butene products can in other embodiments be used to make maleic anhydride. While U.S. Pat. No. 3,907,834 to Milberger et al. or a "Process for Making Maleic Anhydride" (using mixed oxides of antimony and molybdenum) and U.S. Pat. No. 4,240,931 also to Milberger et al. for "Oxidaiton Catalyst" describe processes for converting n-butenes and 1,3-butadiene to maleic anhydride and cite to other, previous descriptions of the same transformation, U.S. Pat. No. 4,075,232 to Zagata et al. observes that two fixed-bed reactors containing two different catalysts had been considered advisable for best yields—with the first reactor being employed to convert n-butenes to butadiene and the second reactor being optimized to convert the butadiene to maleic anhydride, Zagata et al. purported to improve upon the earlier, single catalyst and two fixed bed reactor/two catalyst processes by employing the combination of two catalysts in one, substantially undivided reaction zone in a fluidized reactor. According to Zagata et al., surprisingly the two reactions are compatibly run in the same space and provide substantial yields of maleic anhydride.

Turning now to the propylene product 66, this material can be used in the conventional ways that propylene from fossil fuel processing may be used: polymerization in isotactic, syndiotactic and atactic forms, for oxidation in the presence of ammonia to produce acrylonitrile, to make propylene oxide and its derivatives (glycols, amines and polyether polyols), to make isopropanol, to alkylate benzene and produce cumene thereby, to make acrylic acid for production of acrylate esters, acrylamides and polyacrylates etc., see "Propene", Ullmann's Encyclopedia of Industrial Chemistry, 11th edition, Wiley-VCH Verlag GmbH & Co. KGaA, Wertheim (2012) at pages 1-1.8 and the references cited therein.

The present methods will be further illustrated by the following non-limiting examples:

EXAMPLES

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_{10}O_z$ catalyst by the incipient wetness impregnation method of the '312 application.

The catalyst thus prepared was then placed in a fixed-bed stainless steel reactor having an inside diameter of 5 millimeters, with from 100-800 mg of the catalyst being packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over as half hour. A mixed acetic/propionic aqueous acid feed at a selected molar ratio of aceticpropionic acids was then introduced into an evaporator at 180 degrees Celsius by means of a syringe pump, and the vaporized steam/acid feed was carried into the reactor by a hydrogen and nitrogen gas mixture at a selected hydrogen partial pressure and a particular WHSV on a grams of acetic acid per gram of catalyst per hour basis. The product line was heated to in excess of 150 degrees Celsius before a cold trap, to avoid condensing the liquid products in the product line. A reaction temperature of 415 degrees Celsius was employed for all examples.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

The results of the various examples at two different acetic:propionic acid molar ratios and the same set of hydrogen partial pressures are as shown in Table 1 following:

TABLE 1

Mixed propionic acid and acetic acid to C3-C6 reaction in the presence of hydrogen

| Run # | Reaction temperature (°C.) | $P_{(H2/(H2+N2))}$ | Acetic acid to propionic acid ratio (Molar) | WHSV ($g_{acetic\,acid}$/$g_{catal}$/hr) | Steam to carbon ratio | Acetone selectivity (mol %) | MEK selectivity (mol %) | 3-pentanone selectivity (mol %) | C3 * Selectivity (mol %) | C4 * selectivity (mol %) | C5 * selectivity (mol %) | C6 selectivity (mol %) |
|---|---|---|---|---|---|---|---|---|---|---|---|---|
| 1 | 415 | 0 | 1.0 | 0.07 | 5 | 5.4 | 16.5 | 2.4 | 0.0 | 14.1 | 19.6 | 4.6 |
| 2 | 415 | 10 | 1.0 | 0.07 | 5 | 3.0 | 8.3 | 1.3 | 10.8 | 22.2 | 13.2 | 3.0 |
| 3 | 415 | 40 | 1.0 | 0.07 | 5 | 0.5 | 1.5 | 0.7 | 11.6 | 31.9 | 12.0 | 2.5 |
| 4 | 415 | 80 | 1.0 | 0.07 | 5 | 0.3 | 0.6 | 0.3 | 11.7 | 32.9 | 12.2 | 2.6 |
| 5 | 415 | 0 | 23.4 | 0.28 | 5 | 17.8 | 5.7 | 0.0 | 0.0 | 37.9 | 5.4 | 0.0 |
| 6 | 415 | 5 | 23.4 | 0.28 | 5 | 16.8 | 5.3 | 0.0 | 9.2 | 31.5 | 3.6 | 0.0 |
| 7 | 415 | 10 | 23.4 | 0.28 | 5 | 15.7 | 4.6 | 0.0 | 11.0 | 31.1 | 3.2 | 0.0 |
| 8 | 415 | 20 | 23.4 | 0.28 | 5 | 15.5 | 5.3 | 0.0 | 15.8 | 27.4 | 3.2 | 0.0 |
| 9 | 415 | 40 | 23.4 | 0.28 | 5 | 11.9 | 4.7 | 0.0 | 24.3 | 23.3 | 2.5 | 0.0 |
| 10 | 415 | 80 | 23.4 | 0.28 | 5 | 8.0 | 3.2 | 0.0 | 35.2 | 17.8 | 3.9 | 0.0 |

Whole composition of the reactions:

| Run # | H2O | N2 | H2 | CH4 | Ethylene | Acetone | MEK | 3-pentanone |
|---|---|---|---|---|---|---|---|---|
| 1 | 7.1845% | 92.1053% | 0.0000% | 0.0689% | 0.0093% | 0.0258% | 0.0592% | 0.0069% |
| 2 | 7.1820% | 82.8658% | 9.2073% | 0.1091% | 0.0280% | 0.0144% | 0.0298% | 0.0037% |
| 3 | 7.1812% | 55.2374% | 36.8249% | 0.2038% | 0.0287% | 0.0024% | 0.0054% | 0.0020% |
| 4 | 7.1817% | 18.4139% | 73.6555% | 0.2483% | 0.0244% | 0.0014% | 0.0022% | 0.0009% |
| 5 | 6.7749% | 92.5338% | 0.0000% | 0.0407% | 0.0000% | 0.0804% | 0.0193% | 0.0000% |
| 6 | 6.7739% | 87.8943% | 4.6260% | 0.0542% | 0.0027% | 0.0759% | 0.0180% | 0.0000% |
| 7 | 6.7735% | 83.2632% | 9.2515% | 0.0664% | 0.0041% | 0.0709% | 0.0156% | 0.0000% |
| 8 | 6.7742% | 74.0191% | 18.5048% | 0.0650% | 0.0034% | 0.0700% | 0.0180% | 0.0000% |
| 9 | 6.7735% | 55.5084% | 37.0056% | 0.0664% | 0.0041% | 0.0537% | 0.0159% | 0.0000% |
| 10 | 6.7751% | 18.5073% | 74.0291% | 0.0772% | 0.0197% | 0.0361% | 0.0108% | 0.0000% |

Whole composition of the reactions:

| Run # | IB | Isopentenes | C6 | propene | 1&2-butene | 2-pentene | CO2 |
|---|---|---|---|---|---|---|---|
| 1 | 0.0506% | 0.0563% | 0.0110% | 0.0000% | 0.0000% | 0.0000% | 0.4221% |
| 2 | 0.0405% | 0.0362% | 0.0072% | 0.0517% | 0.0391% | 0.0020% | 0.3832% |
| 3 | 0.0344% | 0.0253% | 0.0060% | 0.0555% | 0.0800% | 0.0089% | 0.3042% |
| 4 | 0.0316% | 0.0264% | 0.0060% | 0.0550% | 0.0850% | 0.0138% | 0.2540% |
| 5 | 0.1284% | 0.0146% | 0.0000% | 0.0000% | 0.0000% | 0.0000% | 0.4079% |
| 6 | 0.1067% | 0.0098% | 0.0000% | 0.0416% | 0.0000% | 0.0000% | 0.3970% |
| 7 | 0.1030% | 0.0087% | 0.0000% | 0.0497% | 0.0020% | 0.0000% | 0.3916% |
| 8 | 0.0891% | 0.0087% | 0.0000% | 0.0714% | 0.0037% | 0.0000% | 0.3726% |
| 9 | 0.0725% | 0.0065% | 0.0000% | 0.1097% | 0.0064% | 0.0005% | 0.3767% |
| 10 | 0.0491% | 0.0076% | 0.0000% | 0.1590% | 0.0115% | 0.0030% | 0.3144% |

* C3 refers to propylene; C4 include isobutene, 1-butene and 2-butene; C5 includes 2-methyl-2-butene, 2-methyl-1-butene, and 2-pentene

What is claimed is:

1. A process for making a product mixture, wherein the process comprises contacting a feed mixture comprising acetic acid and propionic acid with hydrogen in the presence of a $Zn_xZr_yO_z$ mixed oxide catalyst at a temperature in the range of from about 200 to about 700 degrees Celsius and a WHSV ranging from about 0.01 to about 10 hr$^{-1}$ to produce a product mixture comprising isobutene, propylene, 1-butene, 2-butene, 2-methyl-1-butene and 2-methyl-2-butene, wherein a ratio of x:y is from about 1:100 to about 10:1.

2. A process according to claim 1, wherein the $Zn_xZr_yO_z$ mixed oxide catalyst contains less than about 0.14 percent by weight of sulfur.

3. A process according to claim 1, wherein the $Zn_xZr_yO_z$ mixed oxide catalyst contains less than about 0.01 percent by weight of sulfur.

4. A process according to claim 1, wherein the $Zn_xZr_yO_z$ mixed oxide catalyst contains less than about 0.001 percent by weight of sulfur.

5. A process according to claim 1, wherein x:y is from about 1:30 to about 1:1.

6. A process according to claim 5, wherein x:y is from about 1:20 to about 1:5.

7. A process according to claim 6, wherein x:y is from about 1:12 to about 1:10.

8. A process according to claim 1, wherein the feed mixture is or is obtained from a mixed acid fermentation broth from a fermentation of one or more of five carbon sugars, six carbon sugars, lactic acid and lactate substrates, wherein acetic acid and propionic acid are the two most prevalent acids.

9. A process according to claim 1, wherein the feed mixture is obtained by combining a fermentation broth from a fermentation preferentially producing acetic acid and a fermentation broth from a fermentation preferentially producing propionic acid.

10. A process according to claim 1, wherein the feed mixture is obtained from a process for producing 1,2-propanediol by the hydrogenolysis of a feedstock selected from one or more of glycerol, five and six carbon sugars and sugar alcohols, lactic acid and lactate acid in the presence of hydrogen and a suitable hydrogenolysis catalyst and under conditions which are effective for carrying out the hydrogenolysis and in which at least some ethylene glycol is also produced, by dehydrating and oxidizing at least part of the ethylene glycol to form acetic acid and dehydrating and oxidizing at least part of the 1,2-propanediol to form propionic acid, then combining at least some of the acetic acid thus formed with at least some of the propionic acid thus formed.

11. A process according to claim 1, further comprising separating the product mixture to provide a propylene product, a $C_4$ product including isobutene, 1-butene and 2-butene, and a $C_5$ product including 2-methyl-1-butene and 2-methyl-2-butene.

12. A process according to claim 11, further comprising catalytically converting 2-methyl-1-butene and 2-methyl-2-butene to isoprene.

13. A process according to claim 11, further comprising a separations step performed on the $C_4$ product to separate isobutene in the $C_4$ product from 1-butene and 2-butene in the $C_4$ product.

14. A process according to claim 12, further comprising converting 1-butene, 2-butene or both to 1,3-butadiene through catalytic dehydrogenation or oxydehydrogenation.

* * * * *